United States Patent [19]
Behnke et al.

[11] Patent Number: 4,719,277
[45] Date of Patent: Jan. 12, 1988

[54] LINEAR SEGMENTED POLYURETHANE AND PROCESS FOR ITS PRODUCTION

[75] Inventors: Joachim Behnke, Wuppertal; Christoph Josefiak, Kleinwallstadt, both of Fed. Rep. of Germany

[73] Assignee: AKZO NV, Arnhem, Netherlands

[21] Appl. No.: 396,688

[22] Filed: Jul. 9, 1982

[30] Foreign Application Priority Data

Jul. 11, 1981 [DE] Fed. Rep. of Germany ....... 3127464

[51] Int. Cl.$^4$ ..................... C08G 18/08; C08G 18/18
[52] U.S. Cl. ......................... 528/48; 528/52; 528/59; 528/57; 528/85; 524/726; 524/770; 524/875; 210/500.21
[58] Field of Search ............... 528/59, 57, 85, 52, 528/48; 524/726, 770, 875; 210/500.21

[56] References Cited

U.S. PATENT DOCUMENTS 3,664,979  5/1972  Tanomura et al. ............... 528/59
3,769,245 10/1973  Stewart et al. .................. 521/125
4,148,734  4/1979  Hilterhaus et al. ............... 264/48

Primary Examiner—Morton Foelak
Assistant Examiner—M. L. Moore
Attorney, Agent, or Firm—Michael J. Striker

[57] ABSTRACT

In a process for the production of linear segmented polyurethane by simultaneous reaction of macrodiols, low-molecular diols as chain-lengthener and aromatic diisocyanate, in a solvent in the presence of catalyst, and in the presence of catalytic amounts of a magnesium or calcium salt, an aromatic carboxylic acid macrodiol, monomeric, lower-molecular diol and aromatic diisocyanate are reacted, the macrodiol being used in such amounts as to adjust in the prepared polyurethane a weight ratio of soft segment to hard segment of about 4:1 to 1:4. Preferred embodiments include reaction at temperature from about 70° to 120° C.; use of an inert solvent; and having the concentration of starting material amount to about 10–40% by weight relative to the mixture of starting material and solvent. Also provided are polyurethanes obtained according to this process, having a molecular non-uniformity from 2 to 7. Preferred embodiments include that the polyurethane have an average molecular weight from 60,000 to 250,000. The polyurethanes are useful for the production of membranes, specifically those to be used for sterile filtration or blood oxygenation.

20 Claims, No Drawings

LINEAR SEGMENTED POLYURETHANE AND PROCESS FOR ITS PRODUCTION

BACKGROUND OF THE INVENTION

The invention concerns a process for the production of linear segmented polyurethanes through simultaneous reaction of macrodioles, aromatic diisocyanates and low-molecular monomeric diols as chain-lengthener in an inert solvent according to the so-called one-pot process in the presence of catalysts, polyurethane produced according to this process, as well as uses of such polyurethanes, particularly for the production of membranes.

Polyurethanes belong to a class of polymers which distinguishes by a very great variety. Appropriate choice of starting materials provides practically unlimited possibilities for variation in production. Numerous aliphatic, cycloaliphatic and aromatic polyisocyanates can be used alone or in mixture for construction of the polyurethane. In addition to low-molecular monomeric glycols such as ethyleneglycol, butyleneglycol, also higher molecular weight substances displaying hydroxy end-groups, such as polyester, polyglycol and the like can be employed or used together. By varying the ratio of low-molecular glycol to higher-molecular glycol polyurethane of the most different characteristics can be produced. Polyurethanes, in which building blocks are present in the polymer chain that are composed of the higher-molecular polyester or the higher-molecular glycol and which moreover are connected with segments that arise through the reaction of diisocyanate with the lower-molecular glycol, such as, for example, ethyleneglycol, are also called block polymers or segmented polyurethane.

The multitude of polyurethanes can be increased further through the use of compounds with more than two functions, such as e.g. trifunctional alcohols.

Beyond that, side reactions frequently occur to more or less great extent with the synthesis of the polyurethane, such as e.g. the formation of allophanate, whereby intended or unintended the characteristics of the polyurethane are altered. The number of possibilities in polyurethane chemistry is thereby practically inestimable.

It is also of influence in the production of polyurethane whether it is produced in a mass, that is without use of a solvent, or whether the reaction is performed in a solvent.

When working in a solvent it is possible to proceed in many different ways, including initially preparing a so-called pre-polymer by reaction of a macrodiol with a diisocyanate, and then reacting this with a chain-lengthener. It is often desired to utilize the so-called one-pot process, with which all starting materials, i.e. the polyisocyanate, the macrodiol and the low-molecular glycol are simultaneously reacted. Further possibilities for variation exist when, using the one-pot process, the ratio of NCO to OH groups is variably chosen during the main reaction.

With non-catalyzed one-pot reactions it is frequently necessary to work with an excess of diisocyanate in order to achieve the desired molecular weight. This, however, promotes undesirable side reactions, e.g. allophanate and biuret formation. As a result, the reproducibility of the lengthening is impaired, while separations can also occur.

Influencing factors further to the numerous above mentioned possibilities for variation exist, aside from choice of starting materials. These depend on the use of the most different catalysts. Numerous catalysts are known which have been used for the production of polyurethane. With these not only can the speed of the polyurethane formation be increased, but also, intentionally or unintentionally, the characteristics of the produced products can be altered. Thus, through the use of the most different catalysts, the molecular weight of the product is frequently altered during production of polyurethane. Likewise, molecular weight distribution can be influenced. In addition to catalyzing, the catalysts used not only lead to particular polyurethane formation, but frequently also more or less the most different side reactions such as allophanate formation, trimerisation, and the like, which result in branched, networked and thereby generally heavy or even insoluble products. For mass production, fluctuations in the characteristics of the polyurethane, frequently within relatively broad limits, can come into play. For many purposes of use a product is desired with characteristics precisely adjustable and as uniform as possible. This applies in particular to the field of membranes, the production of which from a prepared polymer has already promoted a relatively complicated technology. Thus, the characteristics of membranes are influenced in great measure through deviations in the thickness of the foils, through coagulation conditions, or through their structure, so that one is not confronted with yet a further uncertainty, namely the structure of the polymerisate. There is, moreover, great interest in providing polymers with constant chemical structure and constant characteristics.

It has already been attempted to produce linear segmented polyurethanes with constant viscosity by adding to the reaction mixture, either from the outset or at a determined stage of the reaction, so-called chain-terminating agents and stabilizers. In this manner, however, it is not possible to obtain reproducible polyurethanes with the same, and as narrow as possible molecular weight distributions. Even by varying the reaction temperature such is achieved only to an unsatisfactory measure. At lower temperatures the reactions take far too long in order to permit an industrially useful production of polyurethane solutions. At higher temperatures both side reactions and construction reactions occur to an undesirable extent. This problem has not previously been solved even through the use of an entire series of catalysts. Numerous catalysts, in particular the very frequently used tertiary amine compounds, no longer display catalytic effectiveness in polar solvents at higher temperatures. Many catalysts, such as e.g. organic tin compounds, are toxic and therefore little suitable for polyurethane membranes used for medically related purposes.

Numerous catalysts are mentioned in the article by L. Thiele "Isocyanatreaktion und Catalyse in der Polyurethanchemie", Act. Polymerica 30 (1979), Vol. 6, pp. 232–242, which can be used for the production of polyurethanes. The catalysts mentioned there, however, do not provide the advantages according to the present invention.

U.S. Pat. No. 3,769,245 describes the production of polyurethane foams in the melt. Isocyanate groups are supposed to be reacted with carboxyl groups, and as catalyst preferably magnesium acetate should be used. Magnesium acetate is however completely unsuitable as catalyst for the process according to the present invention.

Acids mentioned, which form with the most different metals salts that are supposed to be suitable for the theredescribed process, are predominantly aliphatic acids, which likewise provide no catalysts useful for the process according to the present invention. Indication that the peripherally mentioned benzoates and naphthates, particularly calcium- or magnesium benzoate or -naphthate, should make possible the production of polyurethanes or polyurethane solutions with the desired characteristics, is not to be found in this reference.

Although already numerous processes for the production of polyurethanes are known, there still exists a need for an improved process for the production of polyurethanes which distinguish particularly by a narrow molecular weight distribution.

SUMMARY OF THE INVENTION

It is therefore an object of the present invention to provide a process for the production of linear segmented polyurethanes, by which polyurethanes can be produced in reproducible manner, and which distinguish by a particularly narrow molecular weight distribution and high molecular weight.

It is an additional object of the present invention to make possible the production of selected reproducible polyurethanes with a determined molecular weight and a corresponding molecular weight distribution.

A further object of the present invention is to make available polyurethanes which can be utilized particularly advantageously for the production of membranes, most specifically those intended for use in the field of medicine.

These objects are attained according to the present invention by a process for the production of linear segmented polyurethanes through simultaneous reaction of macrodiols, lowmolecular diols as chain-lengthener, and aromatic diisocyanates in a solvent in the presence of catalyst, which is characterized by reacting in the presence of catalytic amounts of a magnesium or calcium salt, an aromatic carboxylic acid macrodiol, monomeric, low-molecular diol and aromatic diisocyanate at a temperature of about 70° to 120° C. in an inert solvent, the concentration of starting materials amounting to about 10 to 40% by weight, relative to the mixture of starting material and solvent, and using macrodiol in such amounts as to adjust in the prepared polyurethane a weight ratio of soft segmented to hard segment of about 4:1 to 1:4. Alkyleneglycol with 2 to 4 carbon atoms is particularly suitable as low-molecular diol.

Preferably one uses the starting materials in a concentration of about 14-30% by weight. 4,4'-diphenylmethanediisocyanate is particularly suitable as aromatic diisocyanate. Favorable catalysts include salts of aromatic monocarboxylic acids, of which the benzoic acids, the pyridine-2-carboxylic acids, and the thiophene-2-carboxylic acids are particularly emphasized.

γ-butyrolactone and dimethylacetamide are very suitable solvents for the reaction.

According to a particularly advantageous embodiment of the process according to the present invention, polyalkyleneglycol, preferably polyethyleneglycol and polytetramethyleneglycol, are used as macrodiol. An expedient chain-lengthener is ethyleneglycol.

The polyurethane solutions display advantageously a molecular non-uniformity $U = M_w : M_n$ from about 2 to 7, preferably from about 2 to 5. Their average molecular weight $M_w$ lies preferably in the range from about 60,000 to 250,000, in particular 100,000 up to 150,000.

$M_w$ = mass average molecular weight
$M_n$ = number average molecular weight

The polyurethanes according to the present invention are suitable above all for the production of membranes, in particular membranes for sterile filtration and blood oxygenation.

Performance of the process for the production of polyurethane according to the present invention can follow according to known methods. The so-called one-pot process can be utilized, for which a particularly advantageous embodiment is described e.g. in DE-OS 2 409 789, which is expressly referred to herein.

Starting materials and solvent as pure as possible should be used for the production of the polyurethane solutions. The diisocyanate to be used should display a content of at least 99.0, preferably at least 99.5%. The diisocyanate should not be dimerized and/or trimerized.

Diphenylmethane-4,4'-diisocyanate is particularly suitable as useful aromatic diisocyanate. Also, 1,4-phenylenediisocyanate and tolylenediisocyanate can also be used, among others.

The aromatic diisocyanate can be used alone or in mixture. In many cases it is also possible to substitute a part of the aromatic diisocyanate by aliphatic or cycloaliphatic diisocyanate.

Customary polymers with two preferably terminal hydroxyl groups can be used as macrodiol; more particularly, polyester and polyether. Preferably, polyalkyleneglycol, particularly polyethyleneglycol and polytetramethyleneglycol, are used. The macrodiol employed more expediently displays a molecular weight of about 600 to 20,000. Preferably, the molecular weight of the macrodiol amounts to about 1,000 to 6,000.

The catalyst is generally employed in customary catalytic amounts. It was particularly surprising to find that it is often sufficient within the scope of the present invention to work with only several ppm. The amounts of catalyst used within the scope of the present invention relate to the entire mixture of starting material, i.e. to the employed starting material including the solvent. Weight statements for the catalyst refer to the amount of calcium or magnesium metal. In many cases it can be sufficient to work with about 15 ppm catalyst.

By varying the amount of employed catalyst one can control, in addition to the speed of reaction, also the characteristics of the produced polyurethane. Generally, by increasing the portion of employed catalyst, the uniformity of the produced polymer is improved. The desired narrow polymer distribution is obtained when the amount of catalyst lies in the range of about 10 to 200 ppm.

The amount of employed catalyst depends also on the solvent used. Generally, with amidic solvents such as e.g. dimethylformamide, dimethylacetamide, N-methylpyrrolidone, among others, the required amount is greater than with non-amidic solvents such as e.g. γ-butyrolactone. For amidic solvents preferably 75-200 ppm are used, while for non-amidic solvents preferably about 15-50 ppm catalyst are used. Obviously, still greater amounts can be employed, although for the most part it is not necessary to use more than 1,000 ppm catalyst.

Benzoic acid, 4-nitrobenzoic acid, 4-dimethylaminobenzoic acid, pyridine-2-carboxylic acid, pyridine-3-carboxylic acid, 4-pyridine-4-carboxylic acid, salts of different thiophene acids such as thiophene-2-carboxylic acid, thiophene-3-carboxylic acid, furancarboxylic acid, pyrrolcarboxylic acid, and naphthalene carboxylic acid, among others, may be used as aromatic carboxylic acid which forms useful salts according to the present invention with magnesium or calcium as catalyst.

The salts to be used as catalyts can be produced according to customary processes, e.g. by proceeding from the metal oxide, e.g. magnesium oxide and the acid, and performing the salt formation if necessary in the presence of water or at increased temperature. Subsequent recrystallization is frequently expedient. Since, as already mentioned, the chemical reaction which takes place during production of polyurethane can be very strongly influenced by catalysts, it is obvious within the scope of the present invention that the employed catalysts should be as pure as possible and, in particular, free of free acid. Preferably, the degree of purity of the catalyst should be greater than 95%.

The solvent employed should be inert, i.e. it should not be able to react substantially either with the starting materials, i.e. the diisocyanate and the dihydroxy compounds, or with the polyurethane being formed and the catalyst employed. Suitable solvents include among others dimethylacetamide, γ-butylrolactone and dimethylformamide.

The temperature at which reaction should be performed lies between about 70° and 120° C. At lower temperatures the danger exists that the polyurethane precipitates before conclusion of the reaction. At temperatures above 120° C. undesirable side reactions can occur, also a decomposition of the polyurethane. Preferably, the reaction should be performed according to the present invention in a temperature range between about 70° and 90° C. The temperature to be chosen depends also on the employed solvent. Accordingly, the selected temperature when dimethylacetamide is used lies somewhat lower than when γ-butyrolactone is used. With γ-butyrolactone a most preferred range is 80°-90° C. With dimethylacetamide it is preferred to proceed at 60°-80° C.

Polyesters such as e.g. polyethyleneadipate can be used as macrodiol. Polyalkyleneglycols such as polyethylene- and polytetramethyleneglycol are particularly suitable.

The monomeric, lower-molecular diols ethyleneglycol and butyleneglycol-(1,4) are preferably employed as chain-lengthener. Other diols, such as e.g. hexamethyleneglycol, are also suitable.

In contrast to the macrodiols, non-polymer diols such as e.g. the aliphatic compounds ethyleneglycol, hexamethyleneglycol, butanediol-(1,4) or -(1,3) are to be understood under monomeric, lower-molecular diols.

The ratio of soft segment to hard segment is adjusted to the choice of the ratio between macrodiol and chain-lengthener. Mechanical characteristics of produced membranes, such as strength, elasticity and the like, are influenced by the selected portion of soft segment. This also influences transport characteristics such as permeability.

It is recommended to provide a chain-terminating agent and, if necessary, stabilizer at the end of the reaction or shortly before.

The polyurethane solutions obtained can be used directly for the production of the most different articles, particularly for the preparation of membranes. It is also possible to isolate the polyurethane, by removal of the solvent or by precipitation, and to work it up at a later time, e.g. by re-dissolving in a solvent and forming.

The obtained polyurethane solutions are, however, preferably used directly for the production of membranes, specifically for use in industrial sectors, e.g. for ultrafiltration or sterile filtration, or in medical-related areas, such as e.g. blood oxygenation. An advantageous process for the production of such membranes is described in German Offenlegungsschrift P 29 18 027. Membranes can be prepared from the polyurethane solutions produced according to the present invention by the phase inversion technique. Not only symmetric but also asymmetric membranes can be produced.

If, for example, the polyurethane is separated by evaporation of the solvent, it can be expedient upon further working up to separate any present oligomer portion with a solvent such as alcohol. This is not necessary with the direct working up of the solution for the production of membranes according to the coagulation technique, since in such case the oligomer portion does not remain in the membrane.

It was surprising that according to the present invention polyurethane can be produced in simple manner, which possesses a very narrow molecular weight distribution. It was particularly surprising that with the aid of the process according to the present invention, reproducibly constant molecular weight can be adjusted. The non-uniformity U, i.e. the quotient of the weighted average and the numerical average of the molecular weight, is decreased compared to known polyurethanes. Thus it is possible without more, through the use according to the present invention of catalyst, to reduce the non-uniformity from 15 to 5, in contrast to a process performed under otherwise similar conditions, but without catalyst.

It was particularly surprising that with the use of special catalyst according to the present invention, side reactions are extensively eliminated and in particular, that the undesirable allophanate formation, which otherwise complicates the close of the reaction and leads to networked products, practically do not occur. This is mainly of advantage when membranes must be produced from the polyurethane. The use of diisocyanate in excess is not necessary.

It is moreover very advantageous that with the production of membranes according to the coagulation technique the catalyst employed can be washed out completely or at least to a predominant extent, so that a practically heavy metal-free membrane results. This is of great significance for the medicine-related use of membranes.

This consideration also plays a role with separation processes in the industrial sector, e.g. with sterile filtration, as is done in the foods industry.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

In a thermostatizable 3-liter reaction vessel with stirrer and thermometer, initially 91.44 g polyethyleneglycol 1000 (0.09 Mol) are de-watered at 80° C. in a vacuum for 1 hour. Subsequently 1318 g amine- and water-free dimethylacetamide, 37.92 g (0.61 Mol) ethyleneglycol and 1.5 g magnesiumbenzoate (corresponding 84 ppm Mg, relative to the entire reaction mixture) are added and the solution is heated to 75° C. Within 5 minutes, 175.4 g (0.7 Mol) 4,4'-diphenylmethanediisocyanate is added to this mixture in solid substance. The temperature in the solution rises quickly to about 90° C., and within about 10 minutes it returns again to the thermostat temperature of 75° C. The increase in viscosity of the reaction mixture is traced through the power consumption of the stirrer motor, and is recorded by means of a register. In the course of a further 30 minutes, 5.2 g diphenylmethanediisocyanate, dissolved in 25 g dimethylacetamide, are added dropwise, until the solution is highly viscous. The total reaction period comes to 40 minutes. After addition of 32 g ethanol as chain terminator, the produced polyurethane is precipitated in water, washed and dried. By light scattering in dimethylformamide, the molecular weight is found to be about 144,000 Dalton, the relative viscosity in dimethylformamide amounts to 1.68, and the non-uniformity, measured with a water-gel-permeation chromatograph Model 1200, using 4 styra gel supports, amounts to $$U = \frac{\overline{M_w}}{\overline{M_n}} = 4.1.$$

The relative viscosity is determined in dimethylformamide at 25° C., whereby 0.5 g substance is dissolved and then brought to 100 ml.

COMPARISON EXAMPLE

This example demonstrates the difference between the process according to the present invention and the process which uses another catalyst.

EXAMPLE 2

Analogous to Example 1, a polyurethane is produced, but instead of Mg-benzoate as catalyst 0.73 g Li-benzoate (corresponding 20 ppm Li, relative to the entire reaction mixture) is used. The reaction period amounts to a total 1 hour. Practically no increase in viscosity is observed. The polyurethane isolated from the reaction mixture displays, using gel permeation chromatogram, a maximum for the molecular weight distribution at about 40,000 Dalton, and a non-uniformity of 6.9, whereas the relative viscosity, measured in dimethylformamide, amounts to 1.30.

Further examples are summarized in the following Table. Parameters not specified are as in Example 1.

| Example No. | Catalyst | Amount of Catalyst (g) | Macrodiol MW | Amount (g) | Ethylenglycol (g) | Solvent (g) | Dimethyl-methandiiso-cyanate (g) | Temp. °C. | Viscosity η(rel.) | $\overline{M}_w$ | $U = \dfrac{\overline{M}_w}{\overline{M}_n}$ |
|---|---|---|---|---|---|---|---|---|---|---|---|
| | | | | | | Dimethylacetamid | | | | | |
| 3 |  (O₂N)—⟨benzene⟩—COO)₂Mg | 0.5065 | Polyethylenglycol MW 1000 | 129.9 | 53.9 | 1791.95 | 266.7 (107%) | 75 | 1.60 | 172 000 | 7.8 |
| 4 |  (O₂N)—⟨benzene⟩—COO)₂Mg | 2.21 | Polyethylenglycol MW 1000 | 129.9 | 53.9 | 1791.2 | 269.2 | 75 | 1.59 | 121 000 | 4.3 |
| 5 |  ⟨naphthalene⟩—COO)₂Mg | 2.27 | Polyethylenglycol MW 1000 | 124.9 | 53.9 | 1741.9 | 264.8 (106,25) | 77 | 1.64 | 158 000 | 5.8 |
| 6 |  ⟨thiophene⟩—COO)₂Mg | 1.71 | Polyethylenglycol MW 1000 | 129.9 | 53.9 | 1866.4 | 266.7 | 76 | 1.75 | 160 000 | 5.0 |
| 7 |  ⟨furan⟩—COO)₂Mg | 1.53 | Polyethylenglycol MW 1000 | 129.9 | 53.9 | 1791.9 | 264.2 | 74 | 1.85 | 207 000 | 6.2 |
| 8 |  ⟨pyridine⟩—COO)₂Mg | 1.66 | Polyethylenglycol MW 1000 | 129.9 | 53.9 | 1791.9 | 274.1 | 74 | 1.68 | 183 000 | 6.2 |
| 9 |  ⟨benzene⟩—COO)₂Mg | 1.65 | Polytetramethylenglycol MW 1000 | 129.9 | 53.9 | 1791.2 | 279.2 | 75 | 1.61 | 110 000 | 3.8 |
| | | | | | | γ-Butyrolacton | | | | | |
| 10 | 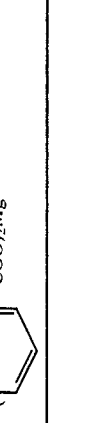 ⟨benzene⟩—COO)₂Mg | 0.308 | Polyethylenglycol MW 1000 | 152.4 | 37.86 | 1647.0 | 194.6 | 90 | 1.49 | 63 000 | 3.7 |
| 11 |  ⟨benzene⟩—COO)₂Mg | 0.308 | Polyethylenglycol MW 1000 | 152.4 | 37.86 | 1647.0 | 198.4 | 90 | 1.58 | 126 000 | 4.8 |

It will be understood that each of the elements described above, or two or more together, may also find a useful application in other types of polymer productions differing from the types described above.

While the invention has been illustrated and described as embodied in linear segmented polyurethanes, process for their production as well as uses for the same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Process for the production of linear segmented polyurethane through simultaneous reaction of macrodiols, low-molecular diols as chain-lengthener and aromatic diisocyanates in an inert solvent in the presence of catalyst, comprising reacting at temperature from about 70° to 120° C. and in the presence of catalytic amounts of a magnesium or calcium salt, an aromatic carboxylic acid, macrodiol, monomeric, low-molecular diol and aromatic diisocyanate, the macrodiol being used in such amounts as to adjust in prepared polyurethanes a weight ratio of soft segment to hard segment from about 4:1 to 1:4.

2. Process according to claim 1, using a concentration of starting materials amounting to between about 10 and 40% by weight relative to combined starting material and solvent.

3. Process according to claim 1, using alkylenediol with 2 to 4 carbon atoms as monomeric, low-molecular diol.

4. Process according to claim 3, using ethyleneglycol as low-molecular, monomeric diol.

5. Process according to claim 1, wherein said starting materials are used in a concentration of about 15–30% by weight.

6. Process according to claim 1, using 4,4-diphenylmathanediisocyanate as aromatic diisocyanate.

7. Process according to claim 1, using an aromatic monocarboxylic acid as catalyst salt.

8. Process according to claim 7, using benzoic acid as catalyst salt.

9. Process according to claim 7, using pyridine-2-carboxylic acid as catalyst salt.

10. Process according to claim 7, using thiophene-2-carboxylic acid as catalyst salt.

11. Process according to claim 1, using γ-butyrolactone as inert solvent.

12. Process according to claim 1, using dimethylacetamide as inert solvent.

13. Process according to claim 1, using polyalkyleneglycol as macrodiol.

14. Process according to claim 13, using polyethyleneglycol as polyalkyleneglycol.

15. Process according to claim 13, using polytetramethyleneglycol as polyalkylene glycol.

16. Polyurethane obtained by the process according to claim 1, characterized by a molecular non-uniformity $U=M_w:M_n=2$ to 7, and having an average molecular weight $M_w$ from about 60,000 to 250,000.

17. Polyurethane according to claim 16, characterized by a molecular non-uniformity U from 2 to 5.

18. Polyurethane according to claim 20, having an average molecular weight $M_w$ from about 100,000 to 150,000.

19. In a process for the production of membranes for sterile filtration or blood oxygenation, of the type in which polyurethane is worked up into membranes by a phase inversion technique, the improvement comprising employing a polyurethane produced according to the process of claim 1, said polyurethane displaying a molecular non-uniformity $U=M_w:M_n=2$ to 7, and having an average molecular weight $M_w$ from about 60,000 to 250,000.

20. In a process for the production of membranes for sterile filtration or blood oxygenation, of the type in which polyurethane is worked up into membranes by a phase coagulation technique, the improvement comprising employing a polyurethane produced according to the process of claim 1, said polyurethane displaying a molecular non-uniformity $U=M_w:M_n=2$ to 7, and having an average molecular weight $M_w$ from about 60,000 to 250,000.

* * * * *